(12) United States Patent
Dogadina et al.

(10) Patent No.: US 6,184,214 B1
(45) Date of Patent: Feb. 6, 2001

(54) PHARMACEUTICAL FORMULATIONS

(75) Inventors: Albina V. Dogadina; Igor E. Gourevitch; Boris I. Ionine, all of St. Petersburg (RU)

(73) Assignee: ITC Research Limited, Staffordshire (GB)

( * ) Notice: Under 35 U.S.C. 154(b), the term of this patent shall be extended for 0 days.

(21) Appl. No.: 09/308,227

(22) PCT Filed: Nov. 21, 1997

(86) PCT No.: PCT/GB97/03203

§ 371 Date: Jul. 6, 1999

§ 102(e) Date: Jul. 6, 1999

(87) PCT Pub. No.: WO98/22479

PCT Pub. Date: May 28, 1998

(30) Foreign Application Priority Data

Nov. 21, 1996 (GB) .................................................. 9624188

(51) Int. Cl.[7] .............................. A61K 31/66; C07F 9/22
(52) U.S. Cl. .............................. 514/75; 562/15; 514/120; 514/134
(58) Field of Search ........................... 514/75, 134, 120; 562/15

(56) References Cited

U.S. PATENT DOCUMENTS

| | | | |
|---|---|---|---|
| 3,940,458 * | 2/1976 | Strong et al. ........................ | 260/943 |
| 4,826,675 | 5/1989 | Gaffer et al. . | |
| 5,395,822 | 3/1995 | Izumi et al. . | |
| 5,707,971 * | 1/1998 | Fahy ....................................... | 514/43 |

FOREIGN PATENT DOCUMENTS

| | | |
|---|---|---|
| 0 085 033 | 8/1983 | (EP) . |
| 0 239 357 | 9/1987 | (EP) . |
| 0 275 198 | 7/1988 | (EP) . |
| 3 246 M | 4/1965 | (FR) . |
| 2043358 | 9/1995 | (RU) . |
| WO 83/02391 | 7/1983 | (WO) . |
| WO 96 40167 | 12/1996 | (WO) . |

OTHER PUBLICATIONS

E. S. Kozlov, Journal of General Chemistry USSR, vol. 56, No. 12, May 20, 1987.
Zidani A et al., Bull. Soc. Chim. Fr., 92, vol. 129 (1), pp. 71–75.
Despax C et al., Tetrahedron Lett, 90, vol. 31, pp. 4471–4472.
Stubbe J A et al., Biochemistry, 72, vol. 11 (3), pp. 338–345.
Sheffer–Dee–Noor S et al., Bioorg. Med. Chem. Lett., 93, vol. 3 (8), pp. 1615–1618.
Kluger R et al., J. Am. Chem. Soc., 84, vol. 106 (14), pp. 4017–4020.
Kenyon G L et al., Biochemistry, 71, vol. 10 (14), pp. 2669–2677.
Benkovic S J et al., J. Amer. Chem. Soc., 71, vol. 93 (10), pp. 2522–2529.
Chemical Abstracts, vol. 109, No. 17, Oct. 24, 1988.
Chemical Abstracts, vol. 113, No. 9, Aug. 27, 1990.
Eur. Surg. Res. 15, pp. 200–207 (1983).
Thorac. Cardiovasc. Surgeon 34, pp. 104–109 (1986).
Scand. J. Thor., Cardiovasc. Surg. 21, pp. 245–249 (1987).
J. Reconstructive Microsurgery vol. 11, No. 6 (1995).
British J. Plastic Surgery 42, pp. 675–681 (1989).

* cited by examiner

Primary Examiner—Charanjit S. Aulakh (57) ABSTRACT

A pharmaceutical composition is provided comprising an effective amount of a phosphoenolpyruvate compound of the formula:

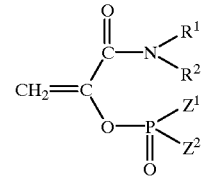

wherein $R^1$ and $R^2$ are independently H, alky, alkenyl, alkoxy (except where applied to $OR^1$), cycloalkyl, aryl, or aralkyl and $Z^1$ and $Z^2$ are independently $OR^1$, or a pharmacologically acceptable salt thereof together with a pharmaceutically acceptable carrier.

34 Claims, 7 Drawing Sheets

PHARMACEUTICAL FORMULATIONS

This application is a 371 of PCT/GB97/03203 filed Nov. 21, 1997 now WO 98/22479 May 28, 1998.

This invention relates to certain amide derivatives of phosphoenolpyruvate (PEP), particularly amide derivatives their uses particularly in preventing ischemic damage to cells, and a method of synthesis for certain amide derivatives and for PEP.

An ischaemic insult results when the blood flow to an organ of the body is insufficient relative to local needs, such that the resulting oxygen supply is greatly reduced. This can result in ischemic damage to the cells and, if the ischaemia is prolonged, to the eventual death of the organ. Ischemia is usually the result of a disease of the blood vessels, such as the arteries supplying the heart, but is also induced during cardiac surgery, involving coronary artery bypass grafting or valve replacements and also transplant operations, typically heart transplants.

Phosphoenolpyruvate (PEP) is a glycolytic substrate which combines with adenosine diphosphate (ADP) to form pyruvate and adenosine-5'-triphosphate acid (ATP), catalysed by the enzyme pyruvate kinase. It is an exergonic reaction which is irreversible under intracellular conditions, requiring $Mg^{++}$ as a cofactor and an alkali-metal cation (e.g. K+) as a physiological activator. The enzyme is activated by increases in glycolytic intermediates such as fructose 1,6-bisphosphate or PEP, or by low ATP concentrations, and is inhibited by high ATP concentrations or when aerobic metabolites such as fatty acids or acetyl CoA are available.

WO83/02391 relates to a pharmaceutical composition for parental administration for preventing and treating ischemic cell damage which comprises a water soluble salt of PEP and a water soluble salt of ATP. Areas of application for the PEP/ATP composition are given as a perfusion and preservation solution for use in open heart surgery and other organ transplants, and for treating ischemic brain and heart damage as a result of heart failure, drowning or drug overdose.

Other scientific publications reporting on the PEP/ATP composition by the same inventors are: Eur. Surg. Res. 15: 200–207 (1983); Thorac. Cardiovasc. Surgeon 34: 104–109, (1986); and Scand. J. Thor. Cardiovasc. Surg. 21: 245–249, (1987). In these papers it is reported that the combination of PEP and ATP in a cardioplegic solution provides better post-ischemic recovery of function (in rat hearts) than PEP alone, but is no better than ATP alone. In J. Reconstructive Microsurgery Vol. 11, no. 6 (November 1995) a PEP/ATP infusion was found to reduce ischemia—repurfusion injury in rabbit skeletal muscle. In another investigation (British J. Plastic Surgery; 42; 675–681 (1989)) it was found that a composition of PEP and ATP or the free radical scavenger SOD, may be useful in the clinical treatment of failing ischemic skin flaps.

PEP has also been suggested to have applications in other areas. Thus, it may be useful in the treatment of physical or mental fatigue (FR-A-3246) in circulatory insufficiencies, as an anticalculus agent (U.S. Pat. No. 4,826,675), as a cosmetic agent in skin preparations, as an anti-tumour agent, and as an agent to enhance the viability of stored blood (EP-A-275198).

In Biochemistry, vol. 11, no. 3 (1972), p338–345, various derivatives of PEP were synthesised and tested as a potential substrate for pyruvate kinase and for enolase. Among the derivatives tested was the dicyclohexylammonium (CHA) salt of α-(Dihydroxyphosphinyloxy)acrylamide, i.e. $CH_2=C[C(O)NH_2]-OP(O)(OH)_2$:2CHA, but it was found that this salt was neither a pseudosubstrate for pyruvate kinase nor a very good competitive inhibitor with respect to phosphoenolpyruvate in the (tested) pyruvate kinase reaction. The synthesis for the dicyclohexylammonium salt as above was given on page 340. The synthetic method used was as follows:

$CH_2=CH-CN---(H_2O_2/NaOH)-->CH_2-CH-C(O)NH_2--$
$(HBr)-->BrCH_2-CH(OH)-C(O)NH_2---(CrO_3)---$
$>BrCH_2-C(O)-C(O)NH_2--(P(OCH_2-Ph)_3)--$
$>CH_2=C[C(O)NH_2]-OP (OCH_2Ph)_2---(1.H_2/Pd;$
$2.2CHA)--->CH_2=C[C(O)NH_2]-OP(O)(OH)_2*2CHA$
i.e. PEP-amide*2CHA (CHA=cyclohexylamine: $C_6H_{11}NH_2$) the actual structure being a salt.

The following other amide derivatives of PEP have been disclosed:
$CH_2=C[C(O)OH]NHP(O) (OH)_2$, Biorganic and Medical Chemistry Letters, no. 3, no. 8, p1615–1618 (1993) (Shani et al); $CH_2=C[C(O)OEt]OP(O) (NMe_2)_2$, $CH_2=C[C(O)OEt]OP(O)MeNMe_2$ $CH_2=C[C(O)OEt]$ $OP(O)OMeNMe_2$; Tetrahedron Letters, Vol. 31, no. 8, p4471 (1990) (Despax et al); $CH_2=C[OP(OH)(OEt)H]$ $C(O)NHR^1$ where $R^1$=Pr or Ph, J. Am. Chem. Soc., Vol. 106, p4017–4020 (1984) (Kluger et al).

There are various syntheses of PEP given in the prior art, such as given in WO83/02391 (see above), and Russian patent no. 2043358 (application no. 92008062/04). In this latter synthesis PEP is formed by oxidative halophosphorylation of a derivative of propenoic acid with $PCl_3/O_2$, followed by dehalogenation of the product then hydrolysis to PEP.

We have now found analogues of PEP as shown in Figure (1) below which have good pharmacological activity; particularly for the prophylaxis or treatment of conditions associated with ischemia:

wherein Z=represents O
  Y=represents $NR^1R^2$ wherein
  $R^1$ and $R^2$ are independently H, alkyl, alkenyl, alkoxy (except where applied to $OR^1$) cycloalkyl, aryl, or aralkyl
  $Z^1$ and $Z^2$ are independently $OR^1$ and pharmacologically acceptable salts thereof.

The compounds of formula 1 and salts thereof are hereinafter "compounds of the invention".

A preferred group of compounds are those of formula (2)

(2)

wherein $R^1$ and $R^2$ are as defined for formula (1).

The more preferred group of compounds within formula (2) is where $R^1$ and $R^2$ are independently H or lower (i.e., $C_{1-5}$) alkyl, such as where $R^1$ is H and $R^2$ is methyl, $R^1$ is H and $R^2$ is ethyl, or where $R^1$ and $R^2$ are both methyl or ethyl.

The most preferred compound is the primary amide of formula (2) (i.e. where $R^1$ and $R^2$ are both H) and salts thereof, particularly the potassium salt, such as the monopotassium salt. The IUPAC name compound is:
2-(dihydroxyphosphoryloxy)prop-2-enoic amide (otherwise known as pyruvic amide enol phosphate). The structure of this compound is shown in formula 3 and hereafter is referred to as "the compound of formula 3" or "compound 3".

By alkyl we include straight and branched chain alkyl groups and the term lower alkyl covers straight and branched alkyl groups having from 1 to 6 carbon atoms, preferably 1 to 4 carbon atoms, such as methyl, ethyl, propyl, isopropyl, butyl, sec-butyl, tert-butyl, pentyl, and hexyl.

Alkenyl refers to an unsaturated or partially saturated hydrocarbon group containing from 2 to 7 carbon atoms which may be straight or branched.

By alkoxy we mean to include alkoxy groups having up to 6 carbon atoms.

Cycloalkyl refers to a hydrocarbon ring having up to 7 carbon atoms.

Aryl refers to any benzenoid aromatic group but preferably phenyl.

Aralkyl refers to an aryl group substituted with one or more alkyl groups.

Preferably the compounds of the invention are administered along with ATP, particularly in the treatment of conditions associated with ischemia.

Examples of physiologically acceptable salts of the compounds of formula (1) and physiologically acceptable derivatives thereof include salts derived from an appropriate base, such as an alkali metal (for example, sodium and potassium), an alkaline earth (for example, magnesium), ammonium and $NX_4^+$ (wherein X is $C_{1-4}$ alkyl) Physiologically acceptable salts of an amino group include salts of organic carboxylic acids such as acetic, lactic, tartaric, malic, isethionic, lactobionic and succinic acids, organic sulphonic acids, such as methanesulphonic, ethanesulphonic, benzenesulphonic and p-toluenesulphonic acids and inorganic acids, such as hydrochloric, sulphuric, phosphoric and sulphamic acids. Physiologically acceptable salts of a compound of a hydroxy group include the anion of said compound in combination with a suitable cation such as $NH_4^+$ and $NX_4^+$ (wherein X is a $C_{1-4}$ alkyl group).

Alkali metal salts are particularly preferred salts of the compounds of formula 2, typically the potassium salt.

The compounds of the invention act to protect and/or aid the recovery of functionally impaired cells such as cardiac tissue, neuronal tissue, organs for transplantation, skin (e.g. failing ischemic skin flaps) and muscle (e.g. skeletal) tissue whose-viability is threatened by hypoxia. The compounds find particular application in preventing, protecting or treating ischaemic cell damage, ischemia or repurfusion injury, such as by using the compound as cardiodrugs and in cardioplegic solutions for open heart surgery. Generally the compounds can be used to protect or preserve any transplant organ or bodily tissue which is under stress or trauma (such as postoperative stress), particularly for aiding myocardial recovery after ischemia. The compounds of the invention function as above even under hypothermic conditions.

Clinical indications which may be treated by the compounds of the invention are myocardial infarction, septic shock, cardiogenic shock (and other manifestations where the heart muscle is depleted of ATP), excision of limbs, indications involving neuronal damage due to cerebral, ischemia and whose damage is due to peripheral vascular ischemia (e.g. as in vascular blockages).

For example the compounds of the invention can be used for treating ischemic brain and heart damage as a result of heart failure, drowning or drug overdose. In such cases the invention could be used in the form of an infusion solution for direct infusion (e.g. via catheters) to treat the damaged organ.

Another area of application for the compounds of the invention is their use in a perfusion and preservative solution for organs, such as in open heart surgery or organ transplantations.

When used in a cardioplegic, perfusion or reperfusion solution for heart surgery, or for organ preservation preferably the concentration of the compounds of the invention (such as the compound of formula 3) is 10 $\mu$mol/L to 50,000 $\mu$mol/L, more preferably 50 $\mu$mol/L to 1000 $\mu$mol/L. For the compound of formula 3, a concentration of 100 $\mu$mol/L has been found to be suitable.

A further important area of application is for blood storage and regeneration, or for rejunenating red blood cells. Thus whereas blood banks can normally only store blood for about 5 weeks, the compounds of the invention, particularly compound 3, can extend the viable storage life of blood. The compounds would suitably be added to the blood (such as in SAG-M media) at a concentration of 10 to 100 $\mu$mol/L preferably 15 to 60 $\mu$mol/L, such as 40 to 60 $\mu$mol/L. A suitable pH range for blood when including compounds of the invention is pH 5.5 to 6.8, such as 6.1 to 6.5.

Early investigations also suggest that the compounds of the invention can be used for cosmetics; as a supplementary drug in tumour treatment; for the treatment of physical and mental fatigue; as an anticalculus or anticaries agent; for the treatment of ageing skin (such as by accelerating keratin turnover); for the treatment of circulatory insufficiencies; as a diagnostic agent for the determination of urea in blood or urine, and for determining cholesterol and triglyceride (U.S. Pat. No. 99,890 incorporated herein by reference); and for enzymatic phosphorylation of natural products such as carbohydrates, glycols, aldehydes, ADP and other nucleotides.

In a second aspect of the invention, there is provided a process for preparing 2-(dihydroxyphosphoryloxy)prop-2-enoic amide, (i.e. the compound of formula (3) which is a primary amide of PEP) and pharmacologically acceptable salts thereof:

(3)

which comprises hydrolysing a compound of formula (4)

(4)

wherein Q is halogen to form said amide, of formula (3). Said amide can be converted into phosphoenolpyruvate enzymatically using a deaminase, or by mild hydrolysis such as by mild alkali (e.g. 0.1N sodium hydroxide). and Said amide or said phosphoenolpyruvate can be converted into a salt thereof. The nitrile of formula (4) is an important intermediate and may also be active.

It is particularly surprising that the cyano group in formula 4 can be hydrolysed to the amide group. This may be attributed to the participation of the juxtaposed phosphoric acid group which is formed from the dihalide of formula 4 during the initial stages of the hydrolysis.

The compounds of formula (4) are prepared by treating a compound of formula (5) with a base (5)

The compounds of formula (5) in turn are prepared by oxidative halophophorylation of acrylonitrile ($CH_2=CH-CN$)

Suitably the oxidative halophosphorylation is carried out using $PCl_3$ in the presence of oxygen (gas) or an oxygen donor compound. Thus Q in the above formulae 4 and 5 is preferably chlorine. The base is preferably a tertiary amine, such as triethylamine.

In a preferred embodiment 2-(dihydroxyphosphoryloxy) prop-2-enoic amide is prepared by the reaction of phosphorus trichloride and oxygen with acrylonitrile followed by HCl elimination and hydrolysis of the formed compound. The reaction of $PCl_3$ and oxygen with acrylonitrile is preferably carried out in relative ratio $PCl_3$:acrylonitrile= 1:5–30 and temperature range from −30 to +50° C. The dehydrohalogenation can be performed with various bases (such as triethylamine and pyridine) in an inert solvent (such as ether, benzene, and carbon tetrachloride). Hydrolysis is carried out by water with or without the presence of an inert solvent (such as ether, benzene, hexane, methylene chloride, or chloroform). When water alone is used, it is best to freeze dry to remove excess water and isolate the product.

Secondary and tertiary amides of PEP, typically those of formula 2, can be prepared as follows.
1. Conversion of PEP amide of formula 3, such as by reaction with thionyl chloride to $CH_2=C[OP(O)Cl_2]$-C(O)Cl followed by reaction with a primary or secondary amine.
2. Oxidative phosphorylation of acryloylchloride, $CH_2=CH-C(O)Cl$, followed by dehydrohalogenation with a tertiary amine to give the trichloride of (1) above, followed by reaction with a primary or secondary amine.

The formulations of the compounds of the inventions include those suitable for oral, parenteral (including subcutaneous, intradermal, intramuscular, intravenous and intraarticular), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of formula (1) and all salts, esters, amides and physiologically acceptable prodrugs thereof ("active ingredient") with the carrier which constitutes one or more accessory ingredients. In general the formulations are prepared by uniformly and intimately bringing into association the active ingredient with liquid carriers or finely divided solid carriers or both, and then, if necessary, shaping the product into the desired formulation.

A typical formulation for the compounds of the invention is a cardioplegic or reperfusion solution, for use in cardiac surgery and transplant operations, and which in addition to a compound of the invention may comprise compounds of sodium, potassium, calcium, magnesium, and buffering agents. More specifically the cardioplegic or reperfusion solution may comprise (in addition to a compound of the invention), sodium chloride, magnesium chloride, potassium chloride, calcium chloride, potassium bicarbonate, and potassium biphosphate.

A formulation used for rejuvenating red blood cells may, in addition to a compound of the invention, contain one or more of sodium or magnesium L-ascorbate phosphate, maltose, mannitol or sucrose, adenine, trisodium citrate, and sodium chloride (to adjust the osmolarity).

Formulations of the present invention suitable for oral administration may be presented as discrete units such as capsules, sachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and nonaqueous sterile suspension which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a base such as gelatine and glycerine or sucrose and acacia.

The compounds of the invention may be administered orally or via injection at a dose range for adult humans of from 5 g to 25 g/day, such as about 15 g/day. Tablets or other forms of presentation provided in discrete units may conveniently contain an amount of compound of the invention which is effective at such dosage or as a multiple of the same, for instance, units containing 500 mg, 1 g or 2 g.

Further aspects of the invention are as follows.

A method for aiding myocardial recovery of a patient after or during an ischemic insult, comprising contacting the cells where ischemia has occurred or will occur by a compound of the invention, particularly a compound of formula 3 and salts thereof.

In a preferred embodiment, the compound of the invention are contained in a cardioplegic solution which is used to arrest and support the heart of a patient undergoing heart surgery, such as coronary artery by-pass surgery or valve replacements or heart transplant surgery (or other organ transplant surgery). Thus in a preferred method, a cardioplegic solution of the invention is used to arrest and maintain the heart during surgery, and the heart is then reperfused with a reperfusion solution. Preferably the reperfusion solution also contains a compound of the invention.

The invention will now be illustrated by way of the following examples.

EXAMPLE 1

2-(dihydroxyphosphoryloxy)prop-2-enoic amide (enol pyruvic amide 2-O-phosphate)—compound of Formula 3

Step 1: Synthesis of dichloride of 1-cyano-2chloroethylphosphoric acid through the oxidative halophosphorylation of acrylonitrile A reactor was charged with acrylonitrile (56 g) and phosphorus trichloride (1050 g), and oxygen was bubbled in, whilst stirring vigorously and with cooling to maintain the temperature at 20° C., at the volume rate of 0.01 m$^3$/h, until the exothermic reaction was complete. Phosphorus trichloride was distilled off under a reduced pressure and the residue was vacuum distilled at ca 1 mm and the product collected as a colourless distillate in the fraction having a boiling point in the range 85–95° C. (139.3 g).

Yield 71% NMR 1H: 3.89 (CH$_2$Cl, JHH 5.0); 5.58 (CH, 3JHP 11.8); NMR 13C: 42.29 (CH$_2$Cl, 3JPC 7.99); 66.42 (CH, 2JPC 7.19); 112.42 (CN, 3JPC 4.63); NMR 31P: 9.11.

Step 2: Synthesis of dichloride of 1-cyanoethenyl phosphoric acid through dehydrohalogenation A solution of the distillate fraction collected from step 1 was added to absolute ether (500 ml), and then triethylamine (26.7 g) in absolute ether (100 ml) was added dropwise at 10° C. After the addition was complete the mixture was stirred for 20 min and the precipitate separated by filtration. The solvent was removed by distillation in vacuo using a water-jet aspirator, and the residue was distilled in vacuo (1 mm) to give the product as a colourless distillate (34.5 g, bp 40° C.). Yield 75% NMR 1H: 6.02 (HA, CHAHB=, 4JAP 3.85, JAB 3.85); 5.94 (HB, CHAHB= 4JBP 3.85); NMR 13C: 120.92 (CH2=, 3JPC 7.34); 125.28 (—C(OP)=, 2JPC 11.72); 111.23 (CN, 3JPC 5.58); NMR 31P 2.32.

Step 3: Synthesis of enolpyruvic amide O-phosphate through hydrolysis

To a stirred solution of dichloride of 1-cyanoethnylphosphoric acid (23.7 g) in 50 ml of chloroform, water (9.5 g) was added dropwise at 30–35° C. After complete addition the reaction mixture was warmed to 40° C. for 20 min to remove HCl. The solvent was removed in vacuo, and acetonitrile (400 ml) was added to the residue. The precipitate was separated and dried in a vacuum to give product as white crystals (12.8 g). Yield 59%. 1H NMR: 5.84 (HA, CHAHB=, 4JAP 2.5, JAB 2.5); 5.43 (HB, CHAHB=, 4JBP 2.5); 13C NMR (solvent CD30D): 105.7 (CH$_2$=); 148.01 (—C(OP)=, 2JPC 8.35); 166.27 (C(O)NH$_2$, 3JPC 8.7); 31P NMR: 4.86.

EXAMPLE 2

Example 1 was repeated, but the final product was obtained as the monopotassium salt of enolpyruvic amide 2-O-phosphate through step 4.

Step 4:

To stirred solution of enolpyruvic amide phosphate (4.4 g) in 50 ml of absolute ethanol, a solution of potassium hydroxide (1.48 g) in absolute ethanol (30 ml) was added dropwise at the temperature 15–20° C. The precipitate formed was separated and vacuum dried to give target compound as white crystals (3.45 g). Yield 75%. 1H NMR: 5.63 (HA, CHAHB=, 4JAP 1.96, JAB 1.96); 5.29 (HB, CHAHB=, 4JBP 1.96); 13C NMR (solvent D20): 104.97 (CH$_2$=, 3JPC 3.07); 147.02 (—C(OP)=, 2JPC 7.89); 167.89 (C(O)NH$_2$, 3JPC 7.24); 31P NMR: −4.58.

EXAMPLE 3

Step 1 of Example 1 was repeated, but using a temperature of 40° C. The yield of dichloride of 1-cyano-2-chlorethylphosphoric was 65%.

EXAMPLE 4

Step 1 of Example 1 was repeated, but using PCl$_3$: acrylonitrile at a ratio 5:1. The yield of dichloride of 1-cyano-2-chlorethylphosphoric was 54%.

EXAMPLE 5

Step 2 of Example 1 was repeated, but using benzene (50 ml) instead of ether. The yield was 60%.

EXAMPLE 6

Step 2 of Example 1 was repeated, but using carbon tetrachloride (100 ml) instead of ether and pyridine instead of triethylamine. Yield 40%.

The above synthesis provides a three step synthesis of 2-(dihydroxyphosphoryloxy)prop-2-enoic amide and some derivatives, in high yield (overall yield 31% in three steps) and high purity (96–99.9%).

The above synthesis can also be used to generate PEP in a convenient way, by simply deaminating the aforementioned amide to PEP such as using a deaminase enzyme, or by mild hydrolysis. Furthermore secondary and tertiary amides can also be prepared via the above route by conversion of the above primary amide to CH$_2$=C[OP(O)Cl$_2$]C(O)Cl followed by reaction with a primary or secondary amine. This is illustrated in Examples 7 to 9.

EXAMPLE 7

React acrylic acid chloride (CH$_2$=CH—COCl) with phosphorus trichloride and oxygen to give the intermediate (1) ClCH$_2$—CH(COCl)OP(O)Cl$_2$ and minor amounts of the phosphonate ClCH$_2$—CH(COCl)P(O)Cl$_2$. Then treat with triethylamine to convert the phosphate (1) to the enolphosphate trichloride (2) CH$_2$=C(COCl)OP(O)Cl$_2$, which can then be purified by fractional distillation. Now treat with one equivalent of various secondary and primary amines followed by two equivalent of water to make amides (3) CH$_2$=C(CONR$^1$R$^2$)OP(O)(OH)$_2$, wherein R$^1$=R$^2$=Et, or Me, and wherein R$^1$=C$_6$H$_{11}$,R$^2$=H.

EXAMPLE 8

Treat the compound of formula 3 of Example 1 with three equivalents of t-potassium t-butoxide to form the tri potassium salt, then add one equivalent of methyl iodide to form the N-methyl analogue of the compound of formula 3—i.e. CH$_2$=CH(CONHMe)OP(O)(OH)$_2$.

EXAMPLE 9

Condense pyruvic acid with diethylamine in the presence of dicyclohexylcarbodiimide (DCC) and N-hydroxysuccinimide to form $CH_3COCONEt_2$. Then convert to the diethylamide of PEP in accordance with the following synthetic route: $CH_3COCONEt_2 \rightarrow LiCH_2COCONEt_2 \rightarrow ClP(O)(OEt)_2 \rightarrow CH_2=C(CONEt_2)OP(O)(OEt)_2 \rightarrow ClSiMe_3 \rightarrow CH_2=C(CONEt_2)OP(O)(OSiMe_3)_2 \rightarrow H_2O \rightarrow CH_2=C(CONEt_2)OP(O)(OH)_2$.

EXAMPLE 10

The phosphate trichloride (1) $ClCH_2—C(COCl)OP(O)Cl_2$ can be converted into the triester $CH_2=C(COOMe)OP(O)(OMe)_2$ by treating the trichloride (1) with excess dry methanol in an excess of triethylamine. The tri ester can then be converted into the mono carboxylic ester $CH_2=C(CO_2Me)OP(O)(OH)_2$ via the silyl ester $CH_2=C(CO_2Me)OP(O)(OSiR_3)_2$.

EXAMPLE 11

Blood Storage/Preservation

Blood was successfully stored for an extended period using the compound of formula 3. The protocol was as follows. Three units of venous blood was taken from three donors and processed with (a) saline-adenine-glucose-mannitol (SAGM)—control (b) SAGM+125 $\mu mol^{-1}$ compound of formula 3 (c) 125 $\mu mol^{-1}$ compound of formula 3. These were then stored at 4° C. Aseptic aliquots were abstracted on days 0, 1, 4, 7, 14, 21, 28, 35, 42 and 49 and assayed for 2, 3 DPG electrolytes, FBC, lactate, methaemoglobin, oxygen dissociation, red blood cell (RBC) ATP assay, RBC morphology and blood culture.

Haemoglobin variants were assayed on day 0 and blood cultures on days 7 and 49.

EXAMPLE 12

A perfusion/reperfusion solution and a cardioplegic solution (according to the invention) for use in Example 8 were made up as follows.

| Krebs Henseleit (KH) buffer - Reperfusion Solutions | | |
|---|---|---|
| Compond | gm/5L | mmol/L |
| NaCl | 34.63 | 118.5 |
| $NaHCO_3$ | 10.50 | 25.0 |
| KCl | 1.75 | 4.75 |
| $MgSO_4.7H_2O$ | 1.48 | 1.19 |
| $KH_2PO_4$ | 0.80 | 1.18 |
| Glucose | 10.0 | 11.0 |
| $CaCl_2.2H_2O$ | 1.04 | 1.4 |

The above compounds are added to a 5 liter volumetric flask, then about 4.5 liters of de-ionised water is added and then gas containing 95% $O_2$:5% $CO_2$ is bubbled through the solution for about 10–15 min. This reduces the pH to 7.4 and prevents precipitation of calcium phosphate when the calcium is added.

After bubbling through the gas $CaCl_2.2H_2O$ is added then volume made up to 5 L and the solution filtered through a 5 $\mu$m filter. Optionally a compound of the invention, preferably the compound of Example 1 (formula 3), is added to the reperfusion solution.

Cardioplegic solution No. 2 (STH2) (as used by St. Thomas' Hospital)
Incorporating PEP-amide of Example 1.

| Stock Solutions (1 liter) | | |
|---|---|---|
| Compond | gm/1L | mmol/L |
| NaCl | 32.142 | 550.0 |
| $MgCl_2.6H_2O$ | 16.25 (32 ml/L) | 80.0** |
| KCl | 5.95 | 80.0 |
| $CaCl_2.2H_2O$ | 0.88 | 60.0 |
| $NaHCO_3$ | 4.2 | 50.0 |
| PEP-amide (from Example 1) | | 0.1 (100 $\mu$mol/L) |

**(for $MgCl_2.6H_2O$ a stock solution made up by dissolving 500 gm (i.e. a new jar of $MgCl_2.6H_2O$ into 1 L de-ionised water).

1L of the cardioplegic solution was made up by adding 200 ml of each of the above stock solutions. This will give a final concentration of each compound of

| Compond | gm/5L | mmol/L |
|---|---|---|
| NaCl | 200.0 | 110.0 |
| $MgCl_2.6H_2O$ | 200.0 | 16.0 |
| KCl | 200.0 | 16.0 |
| $CaCl_2.2H_2O$ | 200.0 | 1.2 |
| $NaHCO_3$ | 200.0 | 10.0 |
| Compound of Example 1 (formula 3) | | 0.1 (100 $\mu$mol/L) |

The pH was then adjusted to 7.8 at 37° C. (by heating on hotplate stirrer) and then the solution filtered through 5 $\mu$m filter.

EXAMPLE 13

Recovery of Heart Function

The cardioplegic solution of Example 12 was compared (as discussed below) against a cardioplegic solution of the monopotassium salt of PEP (PEP-K) in the post-ischemic recovery of rat heart function.

An isolated working rat heart preparation was used. This is a left heart preparation which allows indices of cardiac function to be measured (aortic flow, coronary flow, heart rate, aortic systolic and diastolic pressure) and additional indices to be derived (cardiac output, stroke volume, stroke work). Using this preparation it is possible to simulate cardiopulmonary bypass, incorporating cardioplegic arrest and supportive bypass after ischaemia. The hearts were perfused with Krebs Henseleit buffer (KHB), as prepared in Example 12, containing 95% $O_2$:5% $CO_2$. The hearts were originally perfused in the Langendorff mode for 5 min equilibration and then converted to the working mode for 10 min when measurement of aerobic control function could be made. The hearts were then reconverted to the Langendorff mode for a further 5 min and perfused with either normal KHB or KHB to which the compound of formula 3 (example 1) had been added; they were then converted back to the working mode (again containing either control KHB or KHB plus PEP-amide) for measurement of a second period of control function. The hearts were then arrested with the cardioplegic solution as prepared in Example 12, and subjected to 30 min normotheric global ischaemia and then reperfused with either control KHB or KHB containing the compound of formula 3 in the Langendorff mode for 15 min (simulating supportive bypass). The hearts were then converted to the reperfusate working mode (with reperfusate of either KHB or KHB plus compound formula 3) and post-ischaemic function was measured and expressed as a percent of the pre-ischaemic control function. Finally, the hearts were again converted back to the Langendorff mode for 5 min and then back again to the working mode for a further 15 min when post-ischaemic function was again measured. In this final period hearts were only reperfused with KHB.

Three groups were studied:
1. Hearts were perfused with KHB or normal cardioplegic solution.
2. 100 μmol/L compound formula 3 added to KHB as pretreatment, and to the cardioplegic solution and during initial Langendorff and working mode reperfusion period.
3. 100 μmol/L compound formula 3 added to KHB as pretreatment, and to the cardioplegic solution and during initial Langendorff and working mode reperfusion period.

Recovery of Function

Figure 1:
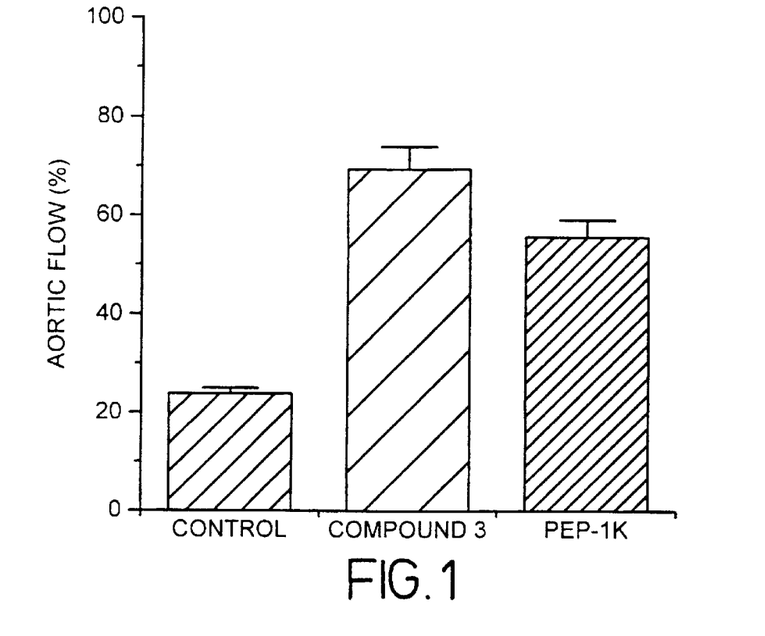
Figure 2:
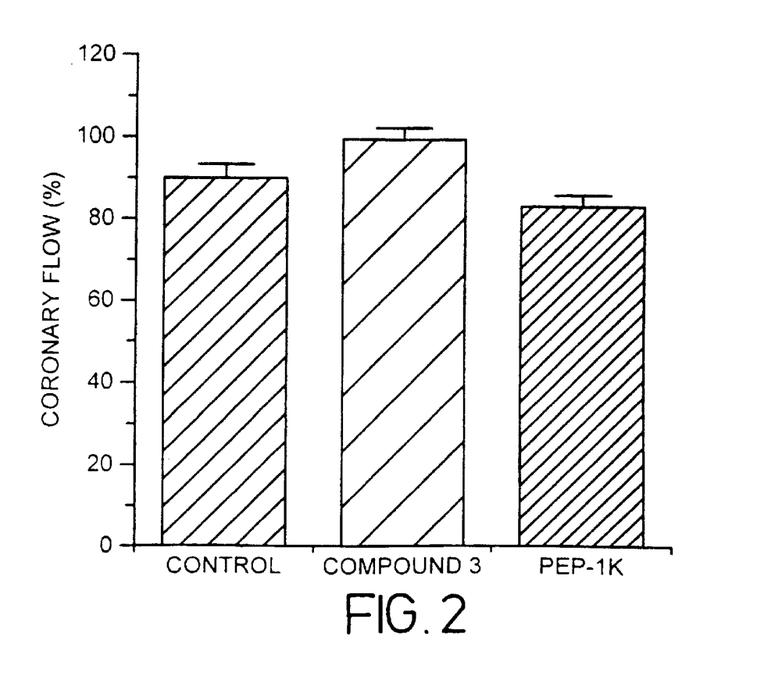
Figure 3:
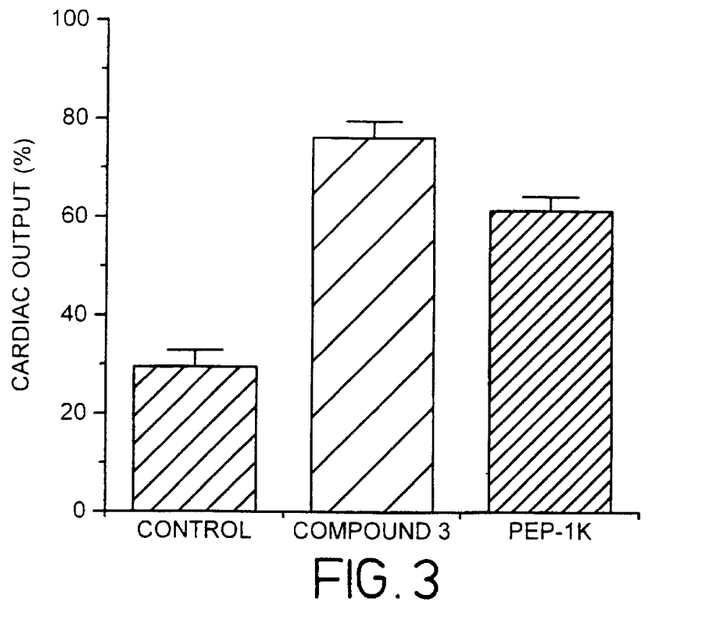
Figure 4:
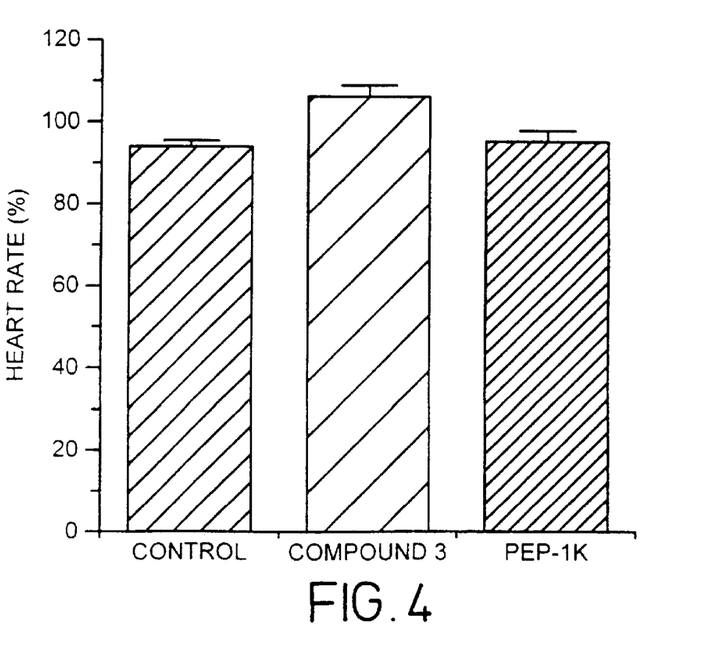
Figure 5:
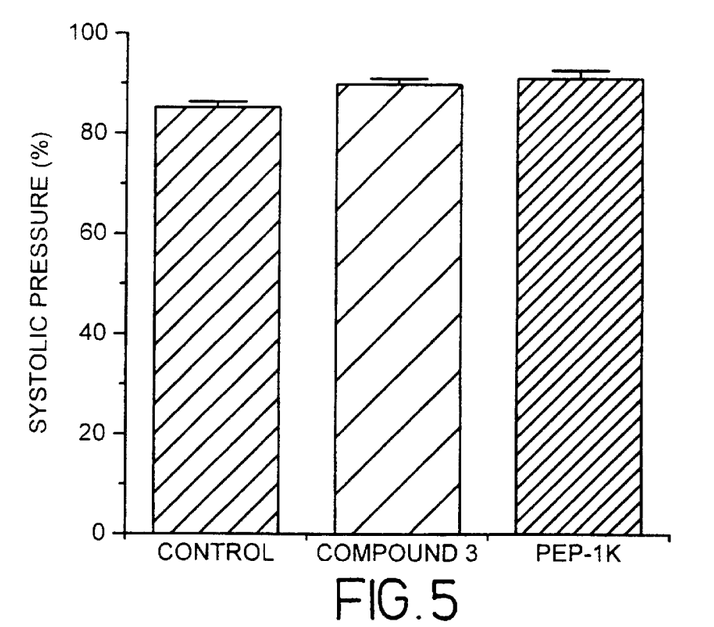
Figure 6:
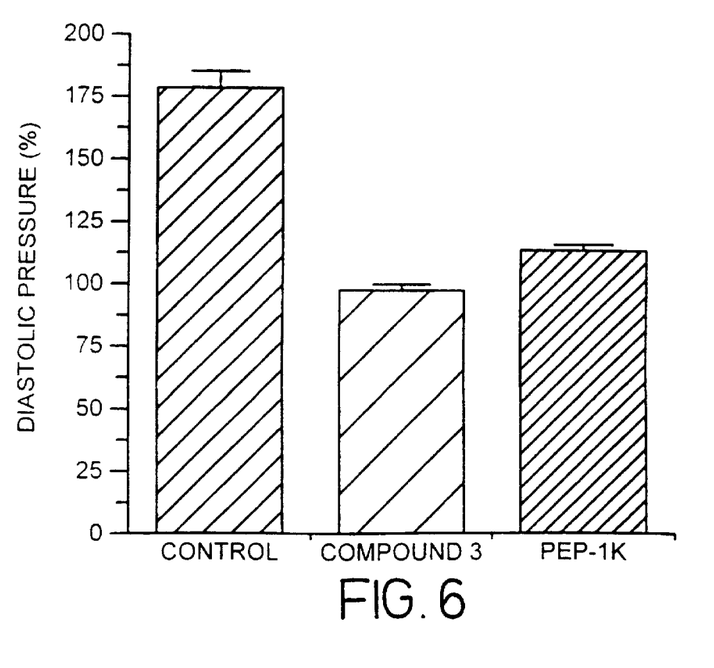
Figure 7:
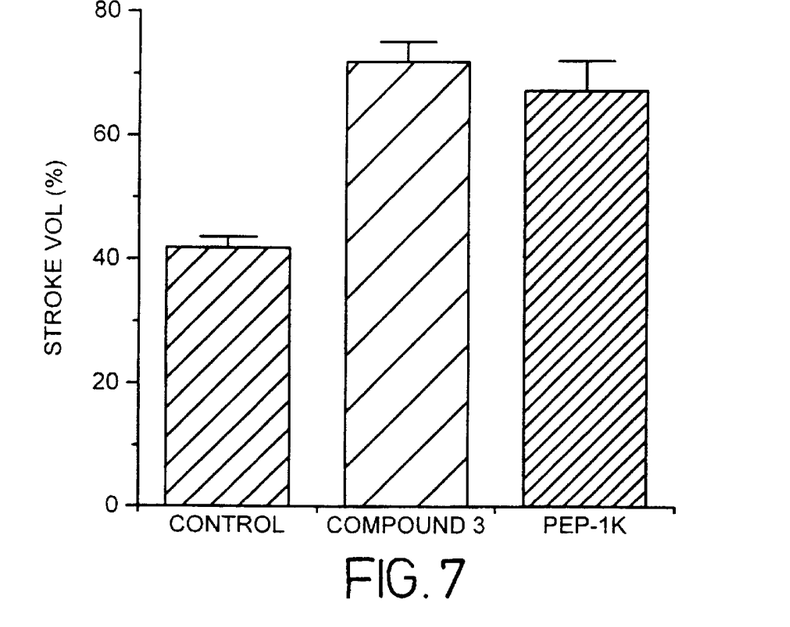
Figure 8:
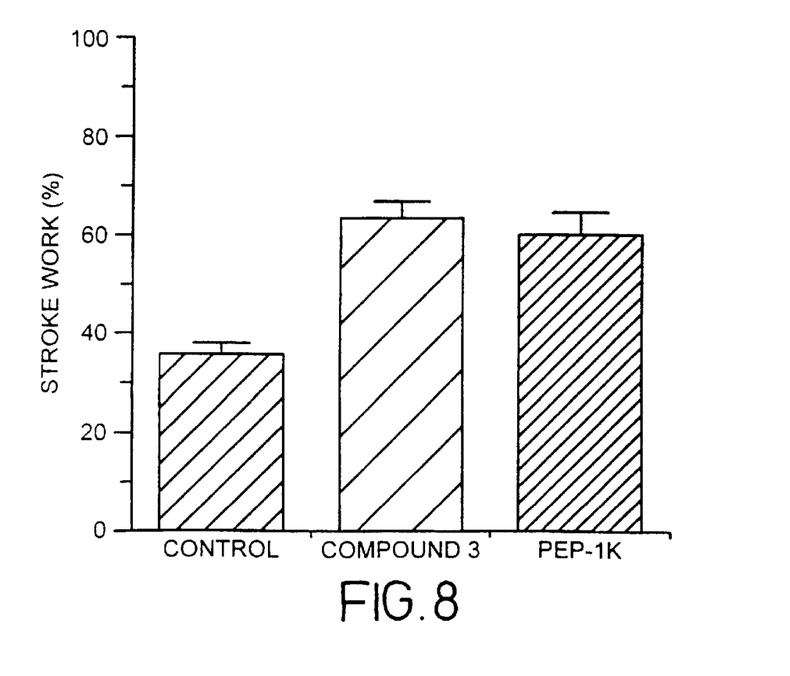
Figure 9:
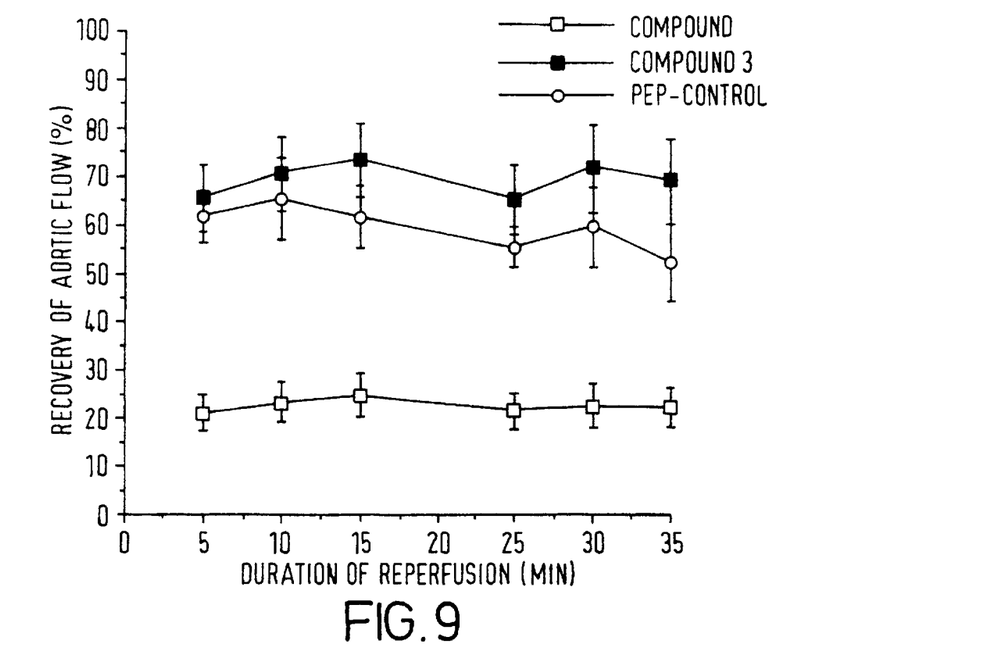
Figure 10:
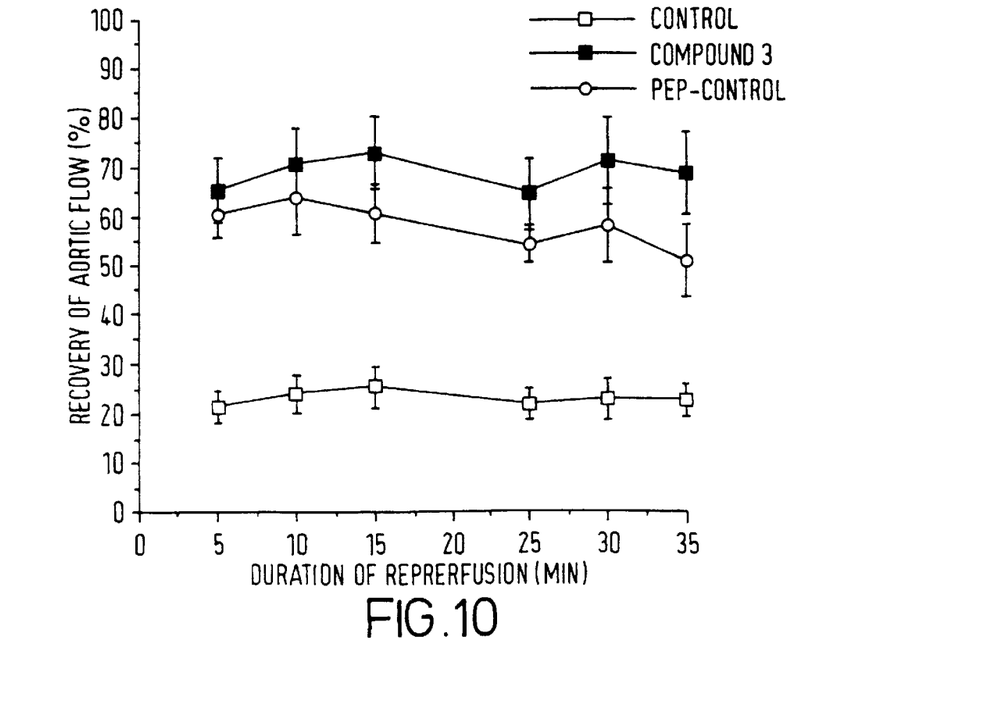

In control hearts the recovery of aortic flow was 23.5±3.5% and compound formula 3 improved recovery to 69.3±4.3%. The heart properties measured for each of the three groups are shown in the accompanying Figures in which Figures 1 to 8 respectively show aortic flow, coronary flow, cardiac output, heart rate, systolic pressure, diastolic pressure, stroke volume, and stroke work. Figures 9 and 10 shows the duration of reperfusion against the recovery of aortic flow at 10 minutes and 20 minutes respectively.

Thus the compound of formula 3, when used as a pretreatment, and/or as an additive to cardioplegic solution and/or as an additive to the reperfusate, significantly enhanced post-ischemic recovery of function when used at a dose of 100 μmol/L. In addition the compound of formula 3 also significantly increased (by approximately 25%) post-ischemic recovery of function over PEP-K.

EXAMPLE 14

Recovery of Function

Figure 11:
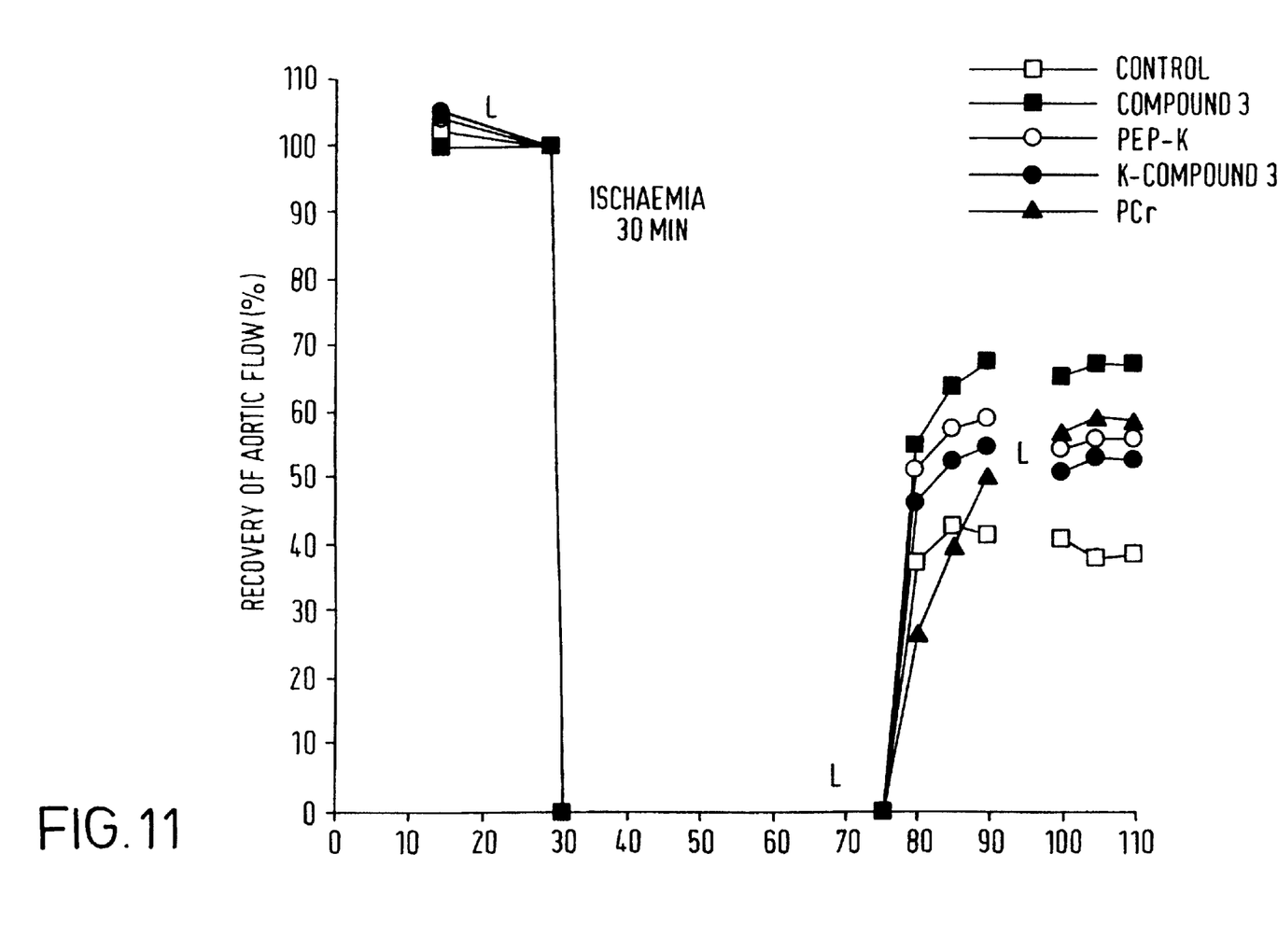
Figure 12:
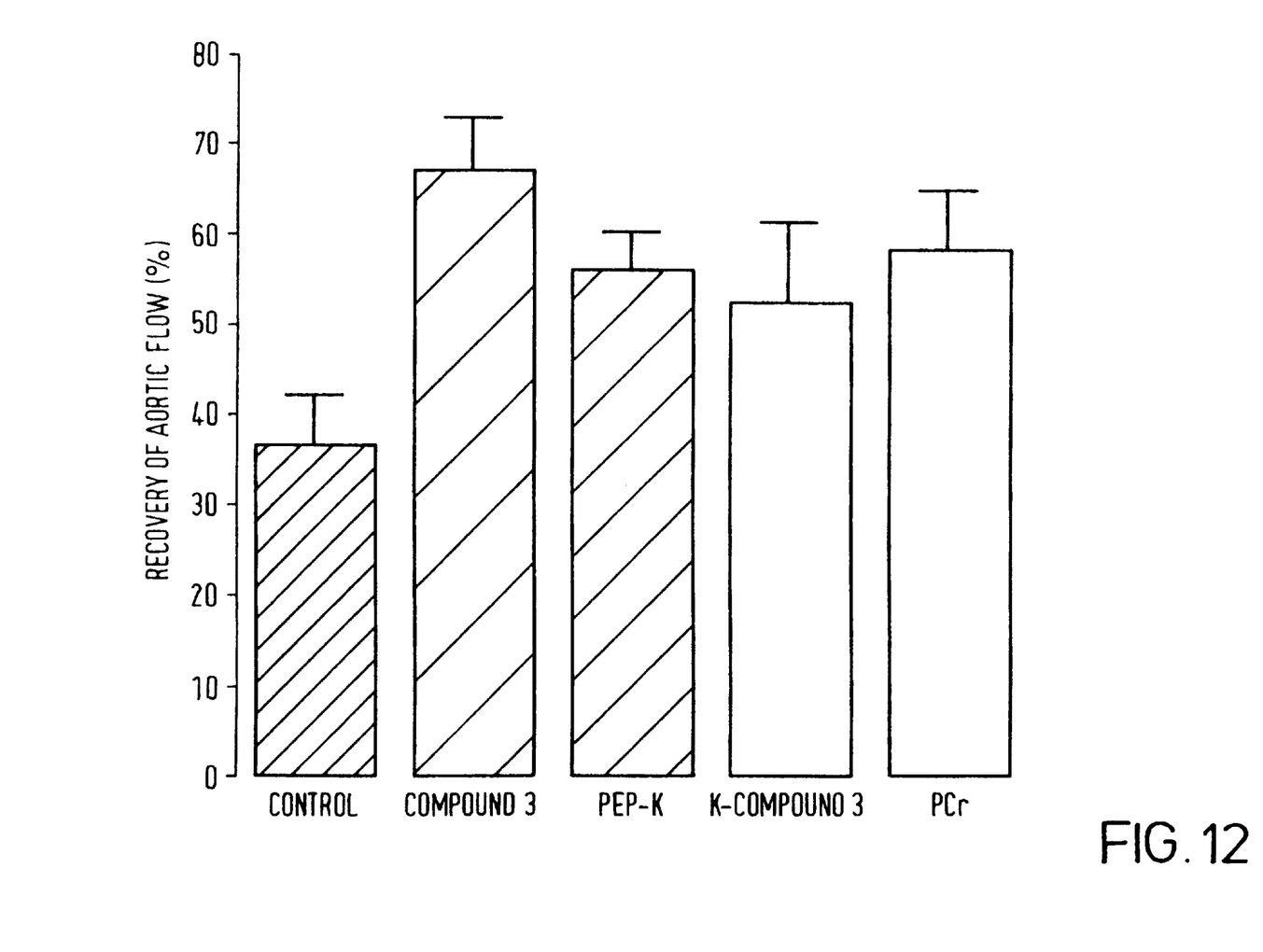

The compound of formula 3 ("compound 3") and its monopotassium salt (K-compound 3) were tested against the following cardioplegic solutions: Langendorff perfusion (control), phosphocreatine (PCr)—the standard/ commercially available treatment, and the monopotassium salt of PEP(PEP-k). The recovery profile during working reperfusion is shown in Figure 11. More particularly Figure 11 shows the recovery profile of aortic flow in control hearts, or hearts treated with 100 μmol/L compound 3, PEP-K, K-compound 3 or 10 μmol/L phosphocreatine (PCr). Langendorff (L) perfusion is shown by the light shaded bars. Results are expressed as a percentage of the mean of the second working period, normalised to 100%. Values are mean (SEM have been omitted for greater clarity). Figure 12 show the percent recovery, after 50 min reperfusion of control hearts and hearts treated with 100 μmol/L compound 3, PEP-K, K-compound 3, 10 μmol/L phosphocreatine (PCr). Values are mean±SEM; *p<0.05.

It can be seen that control hearts, and hearts from compound 3, and K-compound 3 treated groups recover rapidly, reaching a plateau by 10 min of the initial reperfusion period (when, in any of the drug-treated groups, drug would still be present, implying that the drug was not interfering with the rate of recovery of the hearts). These groups of hearts did not improve or deteriorate when the reperfusate was replaced during the second working reperfusion period with KH buffer alone (suggesting that the drug was not interfering with the extent of recovery). This high speed or recovery could be very important in salvaging critical tissue such as of the heart or brain. In contrast, hearts treated with 10 μmol/L PCr recovered slowly and continued to recover throughout the 15 min initial working reperfusion period. These hearts continued to recover when reperfused with KH alone and this recovery did not plateau until the final 10 min of reperfusion. In a clinical situation the optimal administration regime for compound 3 and K-compound 3 may require administration during reperfusion as well as during ischaemia. Figure 12 shows the final recovery (at the end of the 50 min total reperfusion period) for all groups. It is clear that the recovery of hearts treated with compound 3 was significantly (p<0.05) greater than control hearts, and was also greater than the other drug treated groups. K-compound 3, although not as good as compound 3, nevertheless aided recovery to a higher level than the control group.

This study confirms that compound 3 and K-compound 3 as an additive to the pre-ischemic perfusate, to the cardioplegic solution and to the initial reperfusate (also at a dose of 100 μmol/L), significantly improved post-ischemic recovery of function in rate hearts subjected to normothermic global ischemia. In addition, it shows that there was a tendency for hearts treated with compound 3 to recover better than hearts treated with PEP or phosphocreatine. This is even so under hypothermic conditions. Both compound 3 and K-compound 3 also aided a much faster rate of recovery of the hear in the first 10 minutes after administration (Figure 1) than phosphocreatine which may be very important in aiding recovery of function of critical tissue, such as of the heart and brain.

What is claimed is:

1. A process for the preparation of a compound of formula (3):

which comprises hydrolysing a compound of formula (4):

wherein Q is halogen to form said compound of formula (3).

2. The process according to claim 1 wherein said compound of formula (4) is prepared by treating a compound of formula (5) with a base:

wherein Q is halogen.

3. The process according to claim 2 wherein said compound of formula (5) is prepared by oxidative halophosphorylation of acrylonitrile.

4. The process according to claim 2 wherein the base is a tertiary amine.

5. A pharmaceutical composition for treating ischemic conditions due to the lack of ATP comprising an effective amount of a phosphoenolpyruvate compound of the formula (1A):

(1A)

wherein
R$^1$ and R$^2$ are independently H, alky, alkenyl, alkoxy (except where applied to OR$^1$), cycloalkyl, aryl, or aralkyl and
Z$^1$ and Z$^2$ are independently OR$^1$, or a pharmacologically acceptable salt thereof together with a pharmaceutically acceptable carrier.

6. The composition according to claim 5 wherein Z$^1$ and Z$^2$ are OH.

7. The composition according to claim 6 wherein R$^1$ and R$^2$ are independently H or lower alkyl.

8. The composition according to claim 7 wherein R$^1$ and R$^2$ are H.

9. The composition according to claim 5 which is a cardioplegic solution.

10. A method of treating an ischemic condition due to lack of ATP comprising administering to a patient an effective amount of a phosphoenolpyruvate compound of the formula (1A):

(1A)

wherein
R$^1$ and R$^2$ are independently H, alky, alkenyl, alkoxy (except where applied to OR$^1$), cycloalkyl, aryl, or aralkyl and Z$^1$ and Z$^2$ are independently OR$^1$, or a pharmacologically acceptable salt thereof.

11. A method for the treatment or prophylaxis of an ischemic condition due to the lack of ATP selected from the group consisting of myocardial infarction, septic shock, cardiogenic shock and other manifestations where the heart muscle is depleted of ATP, excision of limbs, indications involving neuronal damage due to cerebral ischemia and whose damage is due to peripheral vascular ischemia comprising administering to a patient an effective amount of a phosphoenolpyruvate compound of the formula (1A):

(1A)

wherein R$^1$ and R$^2$ are independently H, alky, alkenyl, alkoxy (except where applied to OR$^1$), cycloalkyl, aryl, or aralkyl and Z$^1$ and Z$^2$ are independently OR$^1$, or a pharmacologically acceptable salt thereof.

12. The method according to claim 11 wherein the condition treated is selected from the group consisting of ischemic brain and heart damage as a result of heart failure, drowning or drug overdose.

13. A method for the treatment or prophylaxis of a condition selected from physical or mental fatigue and circulatory insufficiencies due to the lack of ATP comprising administering to a patient an effective amount of a phosphoenolpyruvate compound of the formula (1A):

(1A)

wherein R$^1$ and R$^2$ are independently H, alky, alkenyl, alkoxy (except where applied to OR$^1$), cycloalkyl, aryl, or aralkyl and Z$^1$ and Z$^2$ are independently OR$^1$, or a pharmacologically acceptable salt thereof.

14. A method of prolonging the viable storage life of stored blood comprising adding thereto an effective amount of a phosphoenolpyruvate compound of the formula (1A):

(1A)

wherein R$^1$ and R$^2$ are independently H, alkyl, alkenyl, alkoxy (except where applied to OR$^1$), cycloalkyl, aryl, or aralkyl and Z$^1$ and Z$^2$ are independently OR$^1$, or a pharmacologically acceptable salt thereof.

15. A pharmaceutical composition comprising an effective amount of a phosphoenolpyruvate compound of the formula (2).

(2)

wherein R$^1$ and R$^2$ are independently H, alkyl, alkenyl, alkoxy, cycloalkyl, aryl, or aralkyl or a pharmacologically acceptable salt thereof together with a pharmaceutically acceptable carrier.

16. The composition according to claim 15 wherein R$^1$ and R$^2$ are independently H or lower alkyl.

17. The composition according to claim 16 wherein R$^1$ and R$^2$ are H.

18. The composition according to claim 5 which is a reperfusion solution.

19. A pharmaceutical composition selected from the group consisting of solid oral dosage units, sterile injection solutions, sterile suspensions, suppositories, lozenges and pastilles and comprising an effective amount of a phosphoenolpyruvate compound of the formula (1A):

(1A)

wherein $R^1$ and $R^2$ are independently H, alkyl, alkenyl, alkoxy (except where applied to $OR^1$), cycloalkyl, aryl, or aralkyl and $Z^1$ and $Z^2$ are independently $OR^1$, or a pharmacologically acceptable salt thereof, together with a pharmaceutically acceptable carrier.

20. The composition according to claim 19 wherein $Z^1$ and $Z^2$ are OH and $R^1$ and $R^2$ are independently H or lower alky.

21. The composition according to claim 20 wherein the phosphoenolpyruvate compound is of the formula (3):

(3)

22. A pharmaceutical composition in unit dosage for administration by a route selected from the group consisting of orally and by injection to provide 5 g to 25 g per day of a phosphoenolpyruvate compound of the formula (1A):

(1A)

wherein $R^1$ and $R^2$ are independently H, alky, alkenyl, alkoxy (except where applied to $OR^1$), cycloalkyl, aryl, or aralkyl and $Z^1$ and $Z^2$ are independently $OR^1$, or a pharmacologically acceptable salt thereof, together with a pharmaceutically acceptable carrier.

23. The composition according to claim 22 wherein $Z^1$ and $Z^2$ are OH and $R^1$ and $R^2$ are independently H or lower alky.

24. The composition according to claim 23 wherein the phosphoenolpyruvate compound is of the formula (3):

(3)

25. The method according to claim 10 wherein $Z^1$ and $Z^2$ are OH and $R^1$ and $R^2$ are independently H or lower alky.

26. The method according to claim 25 wherein the phosphoenolpyruvate compound is of the formula (3):

(3)

27. The method according to claim 11 wherein $Z^1$ and $Z^2$ are OH and $R^1$ and $R^2$ are independently H or lower alkyl.

28. The method according the claim 27 wherein the phosphoenolpyruvate compound is of the formula (3):

(3)

[structure of formula (3)]

29. The method according to claim 13 wherein $Z^1$ and $Z^2$ are Oh and $R^1$ and $R^2$ are independently H or lower alkyl.

30. The method according claim 29 wherein the phosphoenolpyruvate compound is of the formula (3):

(3)

[structure of formula (3)]

31. The method according to claim 14 wherein $Z^1$ and $Z^2$ are OH and $R^1$ and $R^2$ are independently H or lower alkyl.

32. The method according to claim 31 wherein the phosphoenolpyruvate compound is of the formula (3):

(3)

[structure of formula (3)]

33. The method according to claim 32 wherein the pH is in the range 5.5–6.8.

34. A method for the treatment or prophylaxis of cardiac ischemia comprising administering to a patient an effective amount of a phosphoenolpyruvate compound of the formula (3):

(3)

* * * * *

UNITED STATES PATENT AND TRADEMARK OFFICE
CERTIFICATE OF CORRECTION

PATENT NO. : 6,184,214 B1
DATED : February 6, 2001
INVENTOR(S) : Albina V. Dogadina et al It is certified that error appears in the above-identified patent and that said Letters Patent is hereby corrected as shown below:

Claim 5, column 13,
Line 11, change "alky" to -- alkyl --.

Claim 10, column 13,
Line 40, change "alky" to -- alkyl --.

Claim 11, column 13,
Line 62, change "alky" to -- alkyl --.

Claim 13, column 14,
Line 19, change "alky" to -- alkyl --.

Claim 20, column 15,
Line 18, change "alky" to -- alkyl --.

Claim 22, column 15,
Line 31, after "dosage", insert -- form --.
Line 45, change "alky" to -- alkyl --.

Claim 23, column 15,
Line 52, change "alky" to -- alkyl --.

Claim 25, column 15,
Line 65, change "alky" to -- alkyl --.

Claim 29, column 16,
Line 24, change "Oh" to -- OH --.

Signed and Sealed this

Twenty-third Day of October, 2001

Attest:

NICHOLAS P. GODICI
*Acting Director of the United States Patent and Trademark Office*

*Attesting Officer*